(12) United States Patent
Cheng et al.

(10) Patent No.: US 9,566,216 B2
(45) Date of Patent: Feb. 14, 2017

(54) BONE CEMENTS CONTAINING MAGNETIC CALCIUM PHOSPHATE NANOPARTICLES

(71) Applicant: Southwest Research Institute, San Antonio, TX (US)

(72) Inventors: Xingguo Cheng, San Antonio, TX (US); Daniel P. Nicolella, San Antonio, TX (US); Todd L. Bredbenner, Helotes, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 165 days.

(21) Appl. No.: 14/083,215

(22) Filed: Nov. 18, 2013

(65) Prior Publication Data
US 2015/0142112 A1    May 21, 2015

(51) Int. Cl.
  *A61K 6/083*    (2006.01)
  *A61F 2/30*     (2006.01)
  (Continued)

(52) U.S. Cl.
  CPC .............. *A61K 6/0835* (2013.01); *A61F 2/30* (2013.01); *A61K 6/0008* (2013.01);
  (Continued)

(58) Field of Classification Search
  CPC .............. A61F 2310/00023; A61F 2/30; A61F 2/30988; A61F 2/4225; A61F 2/4241; A61F 2/442; A61F 2/4425; A61F 2/4611; A61F 2002/30607; A61F 2002/30624; A61F 2002/30079; A61F 2002/4092; A61F 2002/4096; A61F 2002/4629; A61F 2002/465; A61F 2002/4681;A61F 2002/4683; A61F 2002/30062; A61F 2002/30067; A61F 2002/30131; A61F 2002/30367; A61F 2002/30476; A61F 2002/30563; A61F 2002/30581; A61F 2002/30604; A61K 6/06; A61K 49/1879; A61K 6/083; A61K 6/0835

See application file for complete search history.

(56) References Cited

U.S. PATENT DOCUMENTS 4,728,570 A   3/1988  Ashman et al.
5,783,217 A   7/1998  Lee et al.
              (Continued)

OTHER PUBLICATIONS

Kuhn, K.-D., "Bone Cements, Up-to-Date Comparison of Physical and Chemical Properties of Commercial Materials" Springer-Verlag Publication, 2000, pp. 246-247.

(Continued)

*Primary Examiner* — Christian Sevilla
*Assistant Examiner* — Seema Mathew
(74) *Attorney, Agent, or Firm* — Grossman Tucker et al

(57) ABSTRACT

A bone cement formulation comprising: (a) magnetic calcium phosphate nanoparticles present in an amount of 5.0-95 wt. % and having a largest linear dimension of 150 nm to 50 microns; (b) polymerizable acrylate monomer present in an amount of 5.0-95 wt. %; and (c) polyacrylate polymer present in an amount of 0-80 wt. % and having a largest linear dimension from 5.0 to 500 microns. Upon exposure to an alternating magnetic field the formulation is heated which results in polymerization of the acrylate monomer component. The formulation may also be polymerized via the use of chain polymerization initiators.

18 Claims, 11 Drawing Sheets

(51) Int. Cl.

| | |
|---|---|
| A61K 6/06 | (2006.01) |
| A61K 49/18 | (2006.01) |
| A61L 24/00 | (2006.01) |
| A61K 6/00 | (2006.01) |
| A61K 6/02 | (2006.01) |

(52) U.S. Cl.
CPC .......... *A61K 6/0067* (2013.01); *A61K 6/0082* (2013.01); *A61K 6/0085* (2013.01); *A61K 6/023* (2013.01); *A61K 6/0215* (2013.01); *A61K 6/0235* (2013.01); *A61K 6/06* (2013.01); *A61K 6/0643* (2013.01); *A61K 6/083* (2013.01); *A61K 49/1878* (2013.01); *A61L 24/00* (2013.01); *A61L 2300/44* (2013.01); *A61L 2400/12* (2013.01)

(56) References Cited

U.S. PATENT DOCUMENTS

| | | |
|---|---|---|
| 6,599,498 B1 | 7/2003 | Groman et al. |
| 7,259,210 B2 | 8/2007 | Puckett, Jr. et al. |
| 7,354,995 B2 | 4/2008 | Imamura et al. |
| 7,632,353 B2 | 12/2009 | Hatono et al. |
| 7,678,174 B2 | 3/2010 | Tokuoka et al. |
| 7,976,547 B2 | 7/2011 | Vendrely et al. |
| 8,153,255 B2 | 4/2012 | Furuzono et al. |
| 8,784,384 B2* | 7/2014 | Boyden ............. A61M 37/0015 604/173 |
| 2004/0220672 A1* | 11/2004 | Shadduck ........... A61F 2/30965 623/17.16 |
| 2008/0206296 A1* | 8/2008 | Bouler ................. A61L 24/001 424/422 |
| 2008/0319247 A1* | 12/2008 | Forbes ................... A61N 2/002 600/9 |
| 2009/0221730 A1* | 9/2009 | Kowalski ............ A61L 24/0073 523/116 |
| 2010/0092364 A1 | 4/2010 | Kasinath et al. |
| 2010/0303722 A1* | 12/2010 | Jin ........................... A61L 27/30 424/9.1 |
| 2011/0014296 A1* | 1/2011 | Chen ..................... A61K 9/0009 424/490 |
| 2011/0098374 A1* | 4/2011 | Wichlas ................ A61L 24/001 523/116 |
| 2011/0135577 A1 | 6/2011 | Wu et al. |
| 2013/0150267 A1* | 6/2013 | Roddy ................ C04B 40/0641 507/103 |
| 2013/0210960 A1* | 8/2013 | Lee ..................... A61L 24/0015 523/116 |
| 2014/0044643 A1 | 2/2014 | Cheng et al. |
| 2015/0142112 A1* | 5/2015 | Cheng ................. A61K 6/0008 623/16.11 |

OTHER PUBLICATIONS

Minyuk, P.S. et al, "High-temperature Thermomagnetic Properties of Vivianite Nodules, Lake El'gygytgyn, Northeast Russia", Climate of the Past, 9, pp. 433-445, 2013 [doi: 10.5194/cp-9-433-2013].

Tien, Pei-Lin, et al, Thermal and X-Ray Studies on Earthy Vivianite in Graneros Shale (Upper Cretaceous), Kansas; The American Mineralogist, vol. 54, Sep.-Oct. 1969, pp. 1355-1362.

U.S. Office Action, mail date Jun. 3, 2014 issued in related U.S. Appl. No. 13/568,644.

Pinto, H.P., et al, "First-Principles Studies of Paramagnetic Vivianite Fe3(PO4)2.8H2O Surfaces", Journal of Physical Chemistry C, Chem. C. 2014, 118, pp. 6110-6121.

Wu, H., et al, "Novel Magnetic Hydroxyapatite Nanoparticles as Non-Viral Vectors for The Glial Cell Line-Derived Neurotrophic Factor Gene", Adv. Funct. Mater., 2010, pp. 67-77.

U.S. Office Action, mail date Nov. 9, 2015 issued in related U.S. Appl. No. 13/568,644 (9 pgs.).

Tampieri, A., et al, "Intrinsic Magnetism and Hyperthermia in Bioactive Fe-doped Hydroxyapatite"; Acta Biomaterialia, vol. 8, 2012, pp. 843-851.

Wu, Hsi-Chin, et al, "A Novel Biomagnetic Nanoparticle Based on Hydroxyapatite", Nanotechnology 18 (2007) 165601 (9 pgs) [doi:10.1088/0957-4484/18/16/165601].

Damico, Dennis J., "Reactive Acrylic Adhesives", 2003 Taylor & Francis Group, LLC (38), 13 pgs.

Harris, Craig A., et al., "Metal Artifact Reduction in Musculoskeletal Magnetic Resonance Imaging", Orthopedic Clinics of North America, 2006; 37; pp. 349-359.

Kawashita, M., et al. PMMA-based Bone Cements Containing Magnetite Particles for the Hyperthermia of Cancer; Acta Biomaterialia 6 (2010): pp. 3187-3192.

Kusaka, M, et al, "Effect of hyperthermia by magnetite cement on tumor-induced bone destruction"; Journal of Orthopaedic Science. 2002; 7(3): pp. 354-357.

Li, Z, et al, "In vitro assessment of poly(methylmethacrylate)-based bone cement containing magnetite nanoparticles for hyperthermia treatment of bone tumor"; Journal of Biomedical Materials Research—Part A. 2012;100 A(10): pp. 2537-2545.

Mathieu, JB, et al, "Preliminary investigation of the feasibility of magnetic propulsion for future microdevices in blood vessels"; Bio-Medical Materials and Engineering. 2005;15(5): pp. 367-374.

Mohamed, M., et al, "In situ forming implants for local chemotherapy and hyperthermia of bone tumors"; Journal of Drug Delivery Science and Technology. 2012; 22 (5): pp. 393-408.

Ohura, K., et al. "A heat-generating bioactive glass-ceramic for hyperthermia."; Journal of Applied Biomaterials; 1991; 2(3): pp. 153-159.

Portela, A, et al, "An in vitro and in vivo investigation of the biological behavior of a ferrimagnetic cement for highly focalized thermotherapy"; Journal of Materials Science: Materials in Medicine. 2010;21(8): pp. 2413-2423.

Portela, A, et al. "Highly focalised thermotherapy using a ferrimagnetic cement in the treatment of a melanoma mouse model by low temperature hyperthermia"; International Journal of Hyperthermia. Mar. 2013; 29(2):121-132.

Powell, J., et al, "Numerical simulation of SAR induced around Co—Cr—Mo hip prostheses in situ exposed to RF fields associated with 1.5 and 3 T MRI body coils"; Magnetic Resonance in Medicine. 2012; 68(3): pp. 960-968.

Takegami, K., et al. "New ferromagnetic bone cement for local hyperthermia"; Journal of Biomedical Materials Research. 1998; 43(2): pp. 210-214.

Tang, Z, et al., "Preparation and characterization of PMMA-based cements containing magnetic nanoparticles for the magnetic hyperthermia"; Advanced Materials Research, vol. 647 2013. pp. 155-159.

Alexiou, Christoph et al., "Cancer Therapy With Drug Loaded Magnetic Nanoparticles-magnetic Drug Targeting", Journal of Magnetism and Magnetic Materials 323 (2011) 1404-1407, 2011, 1404-1407.

Denardo, Sally J. et al., "Thermal Dosimetry Predictive of Efficancy of 111 In-ChL6 Nanoparticle AMF-Induced Thermoablative Therapy for Human Breast Cancer in Mice", The Journal of Nuclear Medicine, vol. 48, No. 3, Mar. 2007, Mar. 2007, 437-444.

Farokhzad, Omid C. et al., "Targeted Nanoparticle-Aptamer Bioconjugates for Cancer Chemotherapy In Vivo", Proceedings of the National Academy of Sciences of the United States of America; VI. 103, No. 16, Apr. 18, 2006, 6315-6320, 2006, 6315-6320.

Galanzha, Ekaterina I. et al., "In Vivo Magnetic Enrichment and Multiplex Photoacoustic Detection of Circulating Tumour Cells", Nature Nanotechnology; vol. 4, Published online Nov. 14, 2009; DOI: 10.1038/NNANO.2009.333, Dec. 2009, 855-860.

Hou, Chun-Han et al., "The In Vivo Performance of Biomagnetic Hydroxyapatite Nanoparticles in Cancer Hyperthermia Therapy", Biomaterials, vol. 30, 2009, pp. 3956-3960, 2009, 3956-3960.

Kumar, R. et al., "Chitosan-mediated Crystallization and Assembly of Hydroxyapatite Nanoparticles Into Hybrid Nanostructured Films", Journal of the royal Society Interface, Apr. 2008, vol. 5, No. 21 pp. 427-439; downloaded Jul. 27, 2012 from http://rsif.royalsocietypublishing.org/content/5/211427, 2008, Abstract only.

(56) References Cited

OTHER PUBLICATIONS

Mohapatra, M. et al., "Synthesis and Applications of Nano-Structured Iron Oxides/Hydroxides—A Review", International Journal of Engineering, Science and Technology; vol. 2, No. 8, 2010, 2010, 127-146.

Pareta, Rajesh A. et al., "Increased Osteoblast Density in the Presence of Novel Calcium Phosphate Coated Magnetic Nanoparticles", IOPScience; Nanotechnology 19 (2008) 265101 (7 pgs), 2008, 1-7.

Prakash, K. H. et al., "Wet-chemical Synthesis and Magnetic Property Studies of Fe(III) Ion Substituted Hydroxyapatite", MCB Molecular and Cellular Biomechanics, vol. 3, No. 4, pp. 177-178, 2006, 2006, 177-178.

Salvador-Morales, Carolina et al., "Multifunctional Nanoparticles for Prostate Cancer Therapy", Expert Review of Anticancer Therapy 9[2], 211-221 2009, Corrigendum Correction Notice 9.11 (Nov. 2009); p. 1698, 2009.

Tran, Nhiem et al., "Effects of Magnetite and Maghemite Nanoparticles on Bone Cell and *Staphylococcus aureus* Functions", ingentaconnect, Technology & Innovation, vol. 13, No. 1, 2011, pp. 39-50;, downloaded Jul. 26, 2012 from http://www.ingentaconnect.com/content/cog/ti/2011/00000013/00000001/art00004, 2011, Abstract only.

Tran, Nhiem et al., "Iron Oxide Nanoparticles: Novel Drug Delivery Materials for Treating Bone Diseases", Advanced Materials Research, vol. 89-91, 411, Thermec 2009 Supplement, downloaded on Jul. 26, 2012 from http://www.scientific.net/AMR.89-91.411, 2009, Abstract only.

Wang, Andrew Z. et al., "Superparamagnetic Iron Oxide Nanoparticle-Aptamer Bioconjugates for Combined Prostate Cancer Imaging and Therapy", ChemMedChem 2008; vol. 3, pg. 1311-1315, 2008, 1311-1315.

Wu, Hsi-Chin et al., "A Novel Biomagnetic Nanoparticle Based on Hydroxyapatite", IOPScience, Nanotechnology, 2007, vol. 18, No. 16; Abstract only downloaded on Jul. 26, 2012 from http://iopscience.iop.org/0957-4484/18/16/165601/, 2007, Abstract only.

Zhang, Yan et al., "Magnetic Hydroxyapatite-Encapsulated y-Fe2O3 Nanoparticles Functionalized With Basic Ionic Liquids for Awueous Knoevenagel Condensation", Applied Catalysis A: General 366 (2009) pp. 141-147, Dec. 2009, 141-147.

Li, Z, et al. "Preparation and In Vitro Investigation of Chitosan/nano-hydroxyapatite Composite Used As Bone Substitute Materials", 2005, J. Mater. Sci., pp. 213-219.

Hou, C., et al, "The Fabrication and Characterization of Dicalcium Phosphate Dihydrate-modified Magnetic Nanoparticles and Their Performance in Hyperthermia Processes In Vitro", 2009, Biomaterials, pp. 1-8.

U.S. Office Action, mail date Nov. 6, 2013 issued in related U.S. Appl. No. 13/568,644.

* cited by examiner

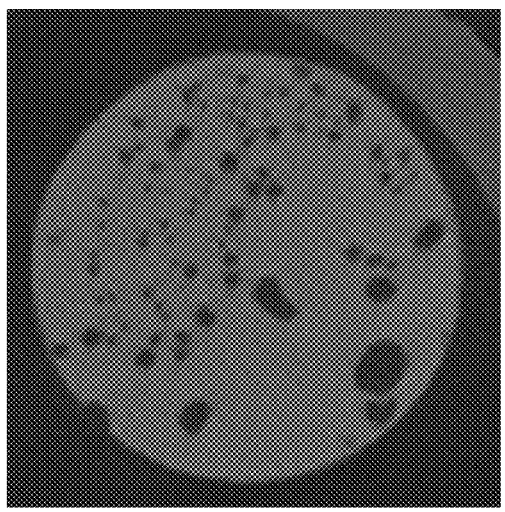 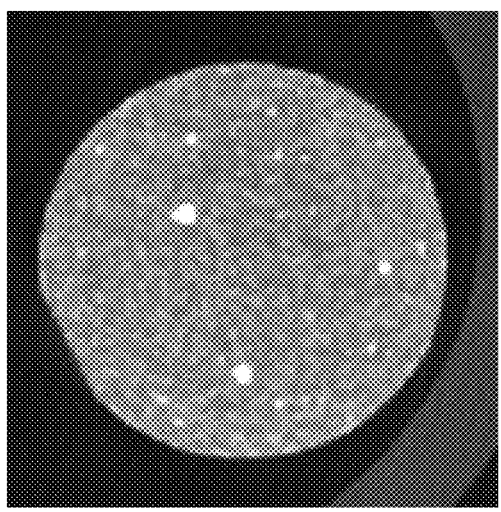
*FIG. 5A*                    *FIG. 5B*

BONE CEMENTS CONTAINING MAGNETIC CALCIUM PHOSPHATE NANOPARTICLES

FIELD OF INVENTION

The present disclosure relates to bone cement formulations containing magnetic calcium phosphate nanoparticles in combination with heat activated polymerization media.

BACKGROUND

Bone is an organic/inorganic composite made from inorganic calcium phosphate (CaP) and organic collagen matrix. The inorganic CaP mainly accounts for the mechanical strength of bone while the organic collagen mainly accounts for the toughness of bone. Due to the presence of inorganic CaP, bone is radio-opaque and can be imaged by X-ray techniques. Bone is a living composite because both the inorganic CaP and collagen are resorbable and can be remodeled (i.e., replaced) by bone cells (osteoblasts, osteoclasts and osteocytes.)

Bone cement is typically based upon an acrylic adhesive made from polymerization of methyl methacrylate (MMA) into poly(methyl methacrylate) (PMMA). Since the 1950s, it has been used to fix joint prosthesis implants within the bone. Many common orthopedic surgical procedures (>1 million per year in the US) such as knee replacement, hip replacement, spinal fusion, and tooth repair require the use of bone cement. However, current commercial bone cements have several drawbacks: (1) PMMA bone cement's relatively poor mechanical properties is one of the factors resulting in implant loosening and failure; and (2) PMMA itself is not a radio-dense material and cannot be imaged by X-ray. The addition of radio-opaque material such as $BaSO_4$ or $ZrO_2$ microparticles (e.g., 10% by weight) in commercial formulations further deteriorates the mechanical properties of bone cement due to relatively weak interfacial bonding (Kuhn K-D, Bone Cements, New York: Springer; 2000. 246-247). In addition, PMMA is non-resorbable and cannot be remodeled by bone cells.

U.S. application Ser. No. 13/568,644 describes the formation of magnetic calcium phosphate particles with diameters in the range of 10 nm to 100 μm, polydispersity in the range of 0.01 to 0.5 and a zeta potential in the range of 1 to 60 mVolts. The particles were preferably formed by co-precipitation of iron oxide and calcium phosphate into particles. The magnetic calcium phosphate particles were utilized to treat, prevent or diagnose a particular disease or condition by administering the magnetic particles to a subject, either alone or included with a selected pharmaceutical formulation. The magnetic particles were capable of being drawn to a specific location by use of magnets, thereby providing the feature of magnetic targeting. In addition, the magnetic particles could be used for imaging and labeling of biological compositions.

SUMMARY

In one embodiment, the present disclosure relates to a bone cement formulation comprising: (a) magnetic calcium phosphate nanoparticles present in an amount of 5.0-95 wt. % and having a largest linear dimension of 150 nm to 50 microns; (b) polymerizable acrylate monomer present in an amount of 5.0-95 wt. %; and (c) polyacrylate polymer present in an amount of 0-80 wt. % and having a largest linear dimension from 5.0 to 500 microns.

In related embodiment, the present disclosure relates to a method for fixing a prosthetic implant to a patient's bone which comprises applying a bone cement formulation to a prosthesis attachment site where the bone cement contains: (a) magnetic calcium phosphate nanoparticles present in an amount of 5.0-95 wt. % and having a largest linear dimension of 150 nm to 50 microns; (b) polymerizable acrylate monomer present in an amount of 5.0-95 wt. %; and (c) polyacrylate polymer present in an amount of 0-80 wt. % and having a largest linear dimension from 5.0 to 500 microns. The bone cement formulation is then exposed to an alternating magnetic field which generates heat in the formulation sufficient to promote polymerization of the polymerizable acrylate monomer.

In a further related embodiment, the present disclosure relates to a method for fixing a prosthetic implant to a patient's bone which comprises applying a bone cement formulation to a prosthesis attachment site. The bone cement contains: (a) magnetic calcium phosphate nanoparticles present in an amount of 5.0-95 wt. % and having a largest linear dimension of 150 nm to 50 microns; (b) polymerizable acrylate monomer present in an amount of 5.0-95 wt. %; and (c) polyacrylate polymer present in an amount of 0-80 wt. % and having a largest linear dimension from 5.0 to 500 microns. This is followed by polymerization of the acrylate monomer. One may include in this formulation chain polymerization initiators and activator compounds that promote formation of free radicals from the initiator.

BRIEF DESCRIPTION OF THE DRAWINGS

The above-mentioned and other features of this disclosure and the manner attaining them will become more apparent and better understood by reference to the following description of embodiments described herein taken in conjunction with the accompanying drawings, wherein:

FIG. 5A is a microcomputed tomography image of a commercial bone cement with PMMA beads.

FIG. 5B is a microcomputed tomograph image of a bone cement composition herein containing magnetic calcium phosphate nanoparticles.

DETAILED DESCRIPTION

The present disclosure is directed at bone cements that contain magnetic calcium phosphate nanoparticles. Reference to a bone cement includes its ordinary meaning and is understood as any material for infilling a bone that includes an in-situ hardenable or settable cement, or a composition that can be infused with such a hardenable cement. As discussed herein, the fill material also can include other "fillers" such as filaments, microspheres, powders, granular elements, flakes, chips, tubules and the like, autograft or allograft materials, as well as other chemicals, pharmacological agents or other bioactive agents.

Magnetic Calcium Phosphate Particles

The magnetic calcium phosphate particles are preferably formed by co-precipitation of iron oxide and calcium phosphate into particles. The iron oxide is included in the crystal lattice (intracrystalline and intercrystalline) and it may not be easily removed under physiological conditions. In addition, calcium phosphate is a natural component of human bone and it is a generally recognized as safe material (GRAS). Accordingly, the magnetic calcium phosphate particle is relatively more biocompatible than iron oxide alone. The magnetic calcium phosphate particles are preferably present at a level of 5.0-95 wt. % at a size (largest linear dimension) of 150 nm-50 microns. Reference to a magnetic calcium phosphate nanoparticle may therefore be generally understood as a particle that is responsive to an applied magnetic field and which, as disclosed herein, causes heating of the surrounding environment containing other chemical components (e.g. monomer or polymer).

Figure 1:
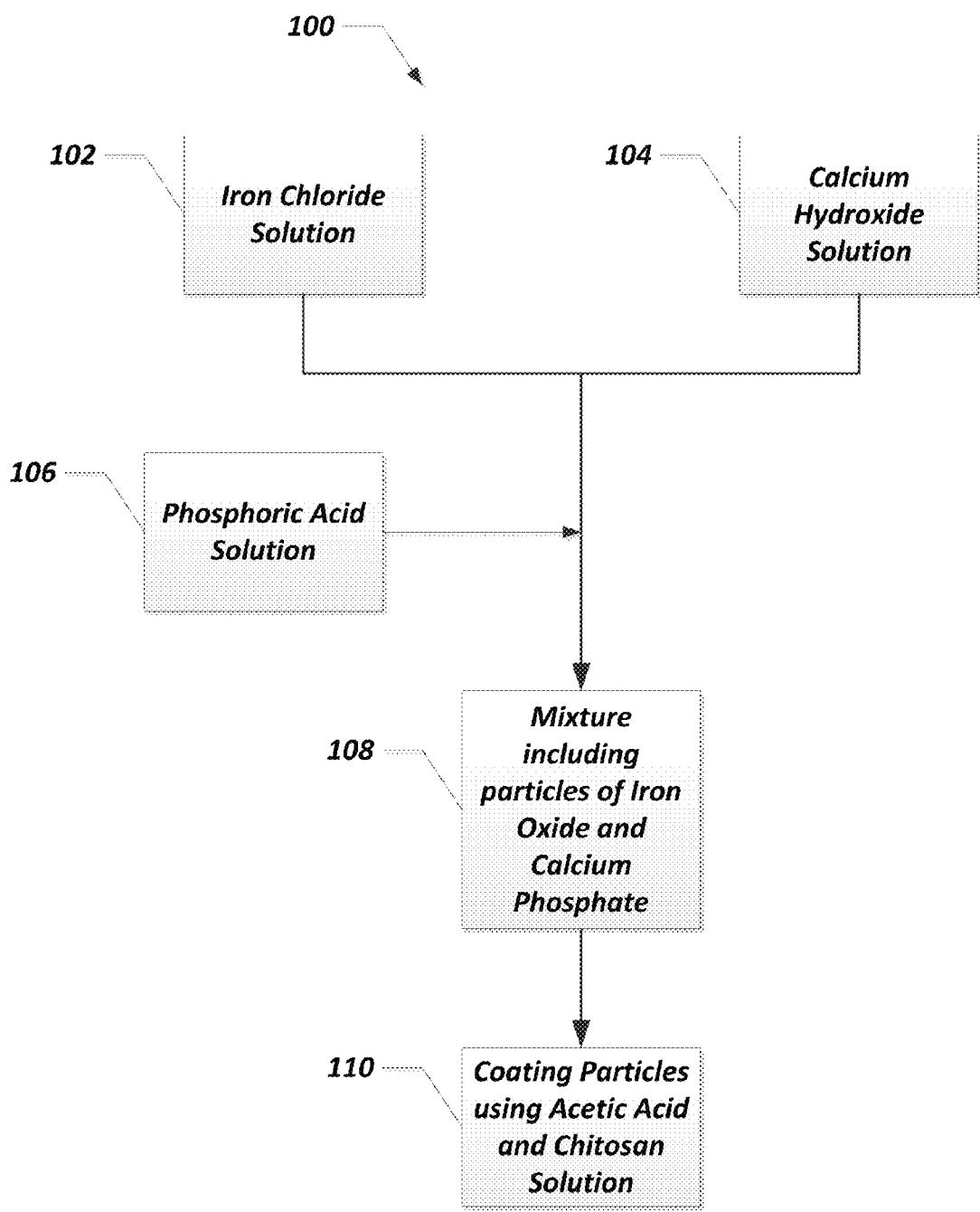
FIG. 1 illustrates a general method of producing magnetic calcium phosphate particles.

FIG. 1 illustrates a general method 100 of producing the magnetic iron oxide/calcium phosphate particles that includes or consists essentially of or consists of combining solutions of iron chloride 102 and calcium hydroxide 104 and adding an inorganic acid such as phosphoric acid 106 to precipitate particles 108 in a mixture, wherein the particles include iron oxide and calcium phosphate. Such particles are responsive to a magnetic field and are understood herein as magnetic calcium phosphate particles.

Figure 2:
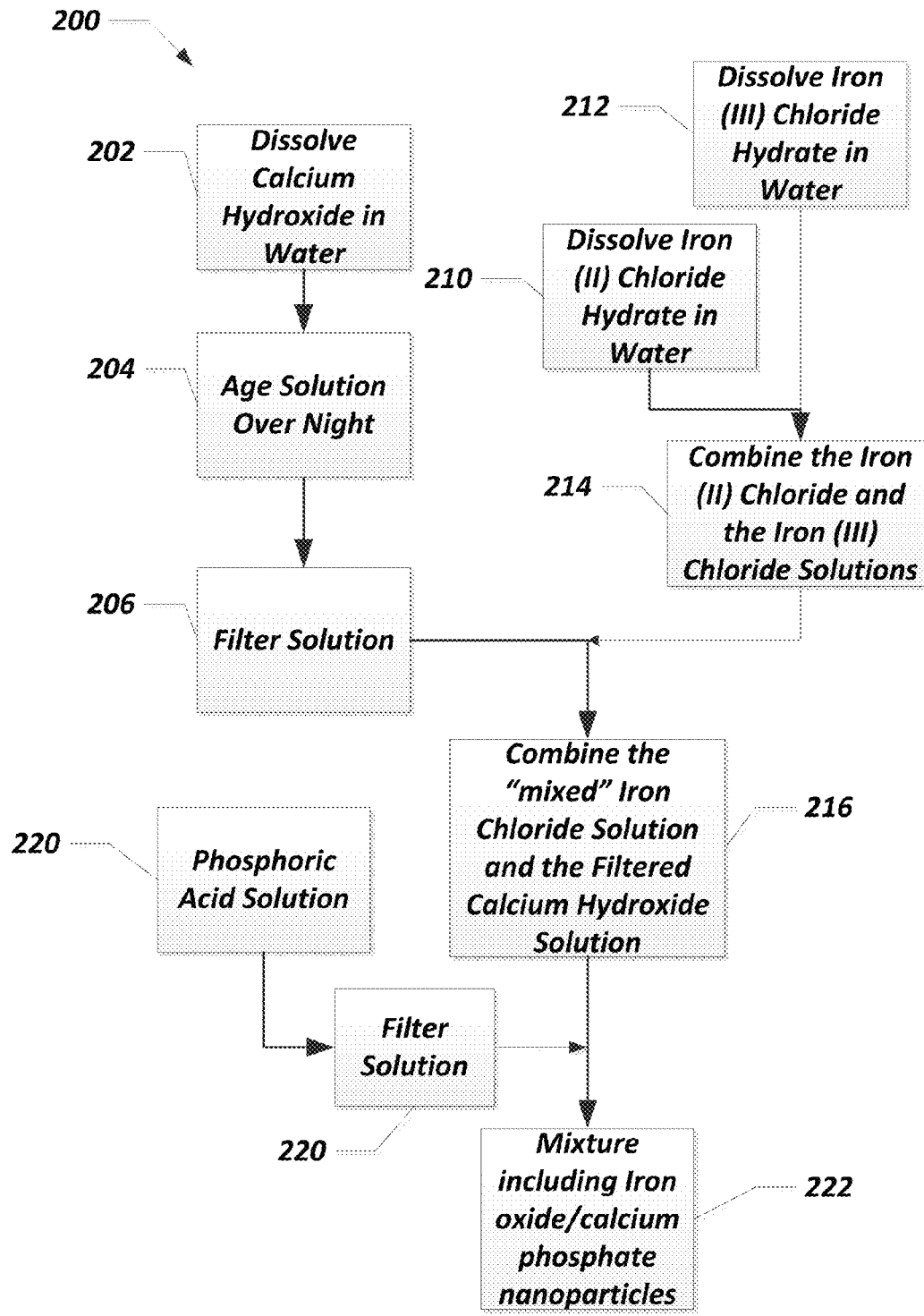
FIG. 2 illustrates a related preparation of magnetic calcium phosphate particles.

FIG. 2 illustrates a related preparation 200 of magnetic calcium phosphate particles involving the combined solutions of the calcium hydroxide solution and the iron chloride solution. The calcium hydroxide solution is prepared by stirring and dissolving calcium hydroxide ($Ca(OH)_2$) in the water 202. The water herein may include, for example, deionized water or nanopure grade water having a resistivity of >18 M$\Omega$/cm$^2$. The calcium hydroxide may be provided at a concentration of 0.001 to 48% by weight (% wt.), relative to the total weight of the solution, including all values and increments therein, such as 2.5% by wt.

The solution may be allowed to age overnight (e.g. between 8 to 24 hours, including all values and increments therein) 204 without agitation. Then the calcium hydroxide solution may be passed through a filter membrane 206 preferably having a porosity of 0.45 µm or less, including all values and increments therein, such as from 100 nm to 450 nm. Particles of calcium hydroxide larger than 0.45 µm are removed from the solution. Removal of larger calcium hydroxide particles may prevent the formation of magnetic calcium phosphate particles that are greater than a desired size, i.e., greater than 1 µm. Accordingly, filtration is considered to be preferable to the process herein of forming the magnetic calcium phosphate particles. After filtration, the concentration of the calcium hydroxide solution may then be measured and verified by stirring the solution well and measuring the density of the solution.

The iron chloride solution may be prepared from two separate iron chloride solutions, a solution of iron (II) chloride and a solution of iron (III) chloride. Specifically, a solution of iron (II) chloride is prepared by dissolving iron (II) chloride hydrate ($FeCl_2.4H_2O$) in water 210. Similarly, a solution of iron (III) chloride is prepared by dissolving iron (III) chloride hydrate ($FeCl_3.6H_2O$) 212.

The concentration of the iron (II) chloride is preferably provided at a mol ratio of 1 mol iron (II) chloride hydrate to 10 mol of calcium hydroxide, based on the measured concentration of the calcium hydroxide after filtration. While calcium hydroxide may therefore be preferably in molar excess to the iron (II) chloride, other molar ratios are contemplated. For example, one may utilize molar ratios of iron (II) chloride to calcium hydroxide of 1:1 to 1:20.

The concentration of the iron (III) chloride is also preferably provided at a mol ratio of 1 mol iron (III) chloride hydrate to 10 mol of calcium hydroxide, based on the measured concentration of the calcium hydroxide after filtration. While calcium hydroxide may therefore preferably be in molar excess to the iron (III) chloride, other molar ratios are contemplated. For example, one may utilize molar ratios of iron (III) chloride to calcium hydroxide of 1:10 to 10:1. The iron (II) chloride solution and iron (III) chloride solution are then combined to obtain a "mixed" iron chloride solution 214, "mixed" meaning a solution containing both species of iron chloride, i.e., iron (II) chloride and iron (III) chloride.

The calcium hydroxide solution and the "mixed" iron chloride solution are then combined and stirred until homogenous 216. The pH of the combined solutions may be in the range of 7 to 12.6, including all values and increments therein, such as a pH of 11.5. The solution may also be dark brown-black in color. The combined calcium hydroxide and "mixed" iron chloride solutions may be brought to a temperature in the range of 30° C. to 100° C., including all values and increments therein and preferably from 35° C. to 45° C. or 40° C., by heating in a water bath while stirring. One may also heat the calcium hydroxide solution to a temperature in the range of 30° C. to 100° C., including all values and increments therein and preferably in the range of 35° C. to 45° C. or 40° C., in a water bath prior to the addition of the "mixed" iron chloride solution to the calcium hydroxide solution.

An inorganic acid, such as a phosphoric acid solution may then be prepared by dissolving phosphoric acid in water 218. The phosphoric acid solution may have a concentration in the range of 1 to 50% weight/volume (% w/v), including all values and increments therein.

The phosphoric acid solution may also be filtered 220. Filtration is accomplished using a first filter having a first pore size in the range of 5 µm or less, such as 5 µm to 0.5 µm, including all values and increments therein. The first filtration is then followed by a second filtration using a second filter having a pore size of 0.45 µm or less, such as 100 nm to 450 nm, including all values and increments therein. Filtration may be facilitated using syringe filters or other filtration mechanisms.

The filtered phosphoric acid solution may be added drop-wise to the combined solutions of the "mixed" iron chlorides and the calcium hydroxide until a pH of 5 to 7, including all values and ranges therein and preferably 5.00, is obtained. The combination of these solutions forms a mixture of magnetic iron oxide calcium phosphate particles 222 which may include $Fe_2O_3$ and/or $Fe_3O_4$ and calcium phosphate $Ca_x(PO_4)_y$, wherein the ratio of x:y may be in the range of 1 to 3. The mixture, including the magnetic calcium phosphate particles, is aged overnight (i.e., 8 to 24 hours, including all values and increments therein) at room temperature, i.e., 21° C. to 25° C., including all values and increments therein.

The resulting particles include mixtures of calcium phosphate with iron oxide and/or encapsulation of iron oxide with calcium phosphate. That is, during the preparation noted above, it has also been observed that when the iron chloride reacts with the calcium hydroxide, the iron oxide may be formed first. Then, after addition of phosphoric acid, the calcium begins to react with the phosphate to form calcium phosphate. Since the iron oxide is already formed, the calcium phosphate may then form on the iron oxide surface to provide an encapsulated structure.

The particles may exhibit a relatively high positive charge, i.e., zeta potential, in the range of 1 to 60 mVolts, including all values and increments therein, such as 50 mVolts. Such zeta potential is understood to indicate, for example, that the particles exhibit good stability in colloidal dispersions. The magnetic calcium phosphate NPs can be separated from water, washed, and lyophilized into dry powder. The dried NPs or NP aggregates can be sieved down to below 50 um for use.

The magnetic calcium phosphate particles produced are now preferably combined with one or more of the following additional ingredients: organic monomers that are subject to polymerization that may be promoted by heat; chain polymerization initiators that are subject to the formation of active initiating compounds for polymerization (e.g. free radicals) upon application of heat; activators (compounds that promote the formation of active initiator compounds from chain polymerization initiators); and/or polymer beads (e.g. PMMA beads). One may also optionally include x-ray contrast agents, one or more drugs, and/or filler type ingredients to strengthen the final bone cement. Further details of these ingredients are provided herein.

Organic Monomers

The organic monomers that are suitable for use herein include any monomer which will preferably undergo polymerization upon exposure to heat. More specifically, upon exposure to heat the monomers may themselves undergo polymerization. In addition, the heat may separately promote the formation of an initiating species (e.g. free-radicals) which then react with the monomer to provide a chain-growth type polymerization.

Preferably, the monomers herein are selected from acrylate monomer structure, which is reference to the following:

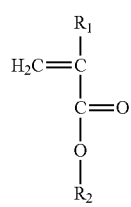

In the above, $R_1$ may comprise a hydrogen or an alkyl group, such as a methyl group ($-CH_3$) or ethyl group ($-CH_2CH_3$). R2 may also comprise an alkyl group or substituted alkyl group, such as a methyl group ($-CH_3$), ethyl group ($-CH_2CH_3$), hydroxyl ethyl ($-CH_2CH_2OH$) propyl ($-CH_2CH_2CH_3$), hydroxyl propyl ($-CH_2CH_2CH_2OH$), or butyl ($-CH_2CH_2CH_2CH_3$). In addition, it should be understood that the monomers may include mixtures of any one of these possible structures. Preferably, the monomer herein is poly(methyl methacrylate), wherein $R_1$ and $R_2$ are both methyl groups.

Accordingly, the acrylic monomer that is employed herein may be selected from methyl methacrylate, butyl methacrylate, butyl methacrylate, triethylene glycol dimethacrylate, carbamate-methacrylate monomers, urethane dimethacrylate, bis-glycidyl methacrylate, ethyl methacrylate, isopropylmethacrylate, 2-hydroxyethyl methacrylate, 3-hydroxypropyl methacrylate, tetrahydrofurfuryl methacrylate, glycidyl methacrylate, 2-methoxyethyl methacrylate, 2-ethylhexyl methacrylate, benzyl methacrylate, 2,2-bis(methacryloxyphenyl)propane, 2,2-bis[4-(2-hydroxy-3-methacryloxypropoxy)phenyl]propane, 2,2-bis(4-methacryloxypolyethoxyphenyl)propane, ethylene glycol dimethacrylate, diethylene glycol dimethacrylate, butylene glycol dimethacrylate, N-vinyl pyrrolidone, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, methacrylic acid, octyl methacrylate, and pentaerythritol tetramethacrylate. The monomer may contain inhibitors such as hydroquinone (HQ) at 0-100 ppm. The monomer is preferably present at a level of 5.0-95.0 wt. %.

Chain Polymerization Initiators and Optional Activators

The chain polymerization initiators herein include those organic compounds which in the presence of heat, will generate active initiating compounds. Preferably, the initiators include free radical type initiators, of which organic peroxides are favored. This may include compounds such as benzoyl peroxide $((PhCOO)_2)$ which can generate two peroxy radicals ($PhCOO^-$). Other contemplated initiators include di-tert-butyl peroxide (tBu-OO-tBu) or methyl ethyl ketone peroxide. The initiators are preferably present at an initiator to monomer ratio of 7-10 wt. %. Suitable activators, if employed, include N,N-dimethyl-p-toluidine (NDMT), N,N-hydroxypropyl-p-toluidine and mixtures thereof. The activator to monomer ratio is preferably 0-2.0% (v/v). For example, one may use 87 uL of NDMT to 4.913 mL of MMA. The activators are designed to facilitate formation of the initiating species. For example, the NDMT may undergo a redox reaction with the organic peroxides and promote radical formation.

Polymer

The polymer that is employed herein is preferably a solid polymer or copolymer particle having a linear dimension from 5.0-500 microns. The polymer may be selected from the corresponding polymer of any of the acrylate monomer structures described herein. Preferably, the polymer is poly (methyl methacrylate). The polymer is preferably present in a range of 0-80.0 wt. %. It may therefore be appreciated that the polymer is an optional ingredient.

Figure 3:
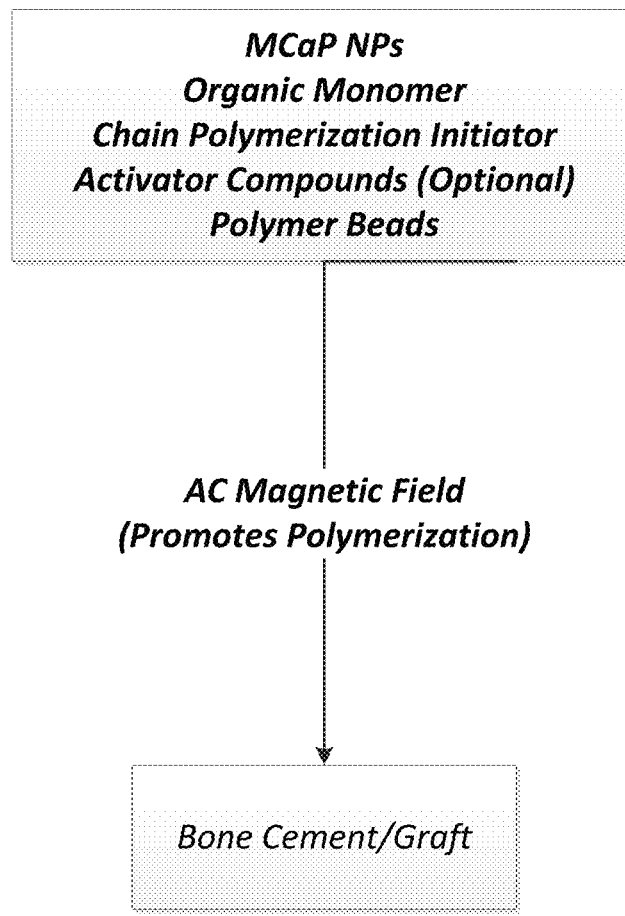
FIG. 3 illustrates the general procedure to incorporate magnetic calcium phosphate particles in a bone cement formulation and apply an AC magnetic field to promote polymerization of the organic monomer component.

The above formulations containing MCaP NPs have been identified as suitable for a magnetic field triggered polymerization. Specifically, with attention to FIG. 3, the MCaP NPs, organic monomer, chain polymerization initiator, activator compound (if present) and polymer beads can be placed within a coil which can produce an alternating magnetic field. The alternating magnetic field preferably is at a frequency of 100 KHz-980 KHz at a field strength of 5 KA/m-40 KA/m. The MCaP NPs will generate heat within such magnetic field and promote either the formation of an active initiating compound and/or the polymerization of the indicated organic monomer. The amount of heat generated may be adjusted based upon the concentration of MCaP NP as well as the strength of the alternating magnetic field applied. Accordingly, the heat generated may provide a preferred temperature rise in the range 20° C.-120° C. The limit of temperature increase is selected such that one preferably avoids vaporization of the monomer.

The process and composition described above offer several advantages over current bone cement systems. As alluded to above, the use of an activator may be completely eliminated through the use of the MCaP NPs formulations noted herein. In such manner, the bone cement formulations herein will avoid polymerization into a hardened state for up to 24 hours at room temperature. That is, the formulations may only polymerize and harden upon application of the alternating magnetic field. Accordingly, the MCaP NP formulations herein offer a relatively longer working time (hours vs. minutes) for the medical professional to apply and manage the bone cement formulations at a selected location in a patient.

While the use of magnetic field can now preferably trigger the polymerization, the formulations herein can also be made to polymerize without the use of an applied magnetic field, similar to the polymerization of a regular bone cement, except that it now contains MCaP NPs. The use of the MCaP NP themselves in the bone cement formulation, aside from providing the ability to generate heat in the presence of an alternating magnetic field, provides other advantages with respect to the interaction of the bone cement within the biological environment. Specifically, the presence of the MCaP NP in the bone cement provides a bone cement that more closely resembles bone composition. That is, as bone tissue incorporates calcium phosphate in the form of calcium hydroxyapatite, the bone cement herein containing MCaP NPs are contemplated to have improved interaction with bone while indicating relatively higher mechanical strength than bone cements that do not contain MCaP NPs.

In addition, due to the presence of the MCaP NPs, the bone cements herein are radio-opaque and can be imaged by x-ray techniques without the need to include a contrast agent. However, optionally, one may add incorporate additive to further enhance the radio-opaque character of the bone cement formulations. Preferably, one may include contrast agents such as barium sulphate ($BaSO_4$) or zirconium dioxide ($ZrO_2$). Such contrast agents may be included at a level of 0-15% by weight.

As noted, the bone cement composition herein may optionally include a drug. The drug can include antibiotics such as gentamycin, tobramycin, vancomycin, or meropenem. The drug may also include a bactericide such as benzalkonium chloride or cetyl pyridinium chloride. One may also include chemotherapy type drugs (cytotoxic antineoplastic drugs). The level of drug in the bone cement, if present, can preferably fall in the range of 1.0-10.0% by weight.

In addition, the bone cement may include other additives. These may include one or more of the following: carbon nanotubes, Au particles, MgO powders, Ti, $TiO_2$, hydroxyl apatite, fibers, and inorganic or organic particulate matter. These other additives may be present at a level of 0-10.0% by weight. For example, it can be appreciated that one may include MgO powder which can increase the mechanical properties (hardness) of the bone cement after polymerization and solidification.

While the bone cements herein are preferably used as bonding materials in the area of bone replacement, bone stabilization and prosthesis securement, the bone cements herein may also be employed for local hyperthermia treatment of, e.g., metastatic bone cancer, bacterial infection, as well as temperature triggered drug release. That is, the bone cements herein may be combined with a drug that is designed for release upon exposure to heat. Accordingly, it is contemplated that the application of an alternating magnetic field and the response of the MCaP NPs in the production of heat may be effectively employed to trigger a release of a selected drug within a patient.

Bone cement formulations are now described in the examples below. These examples are illustrative only and are non-limiting as to the scope of the present invention.

1. Bone Cement Composition & AC Magnetic Fields

Figure 4:
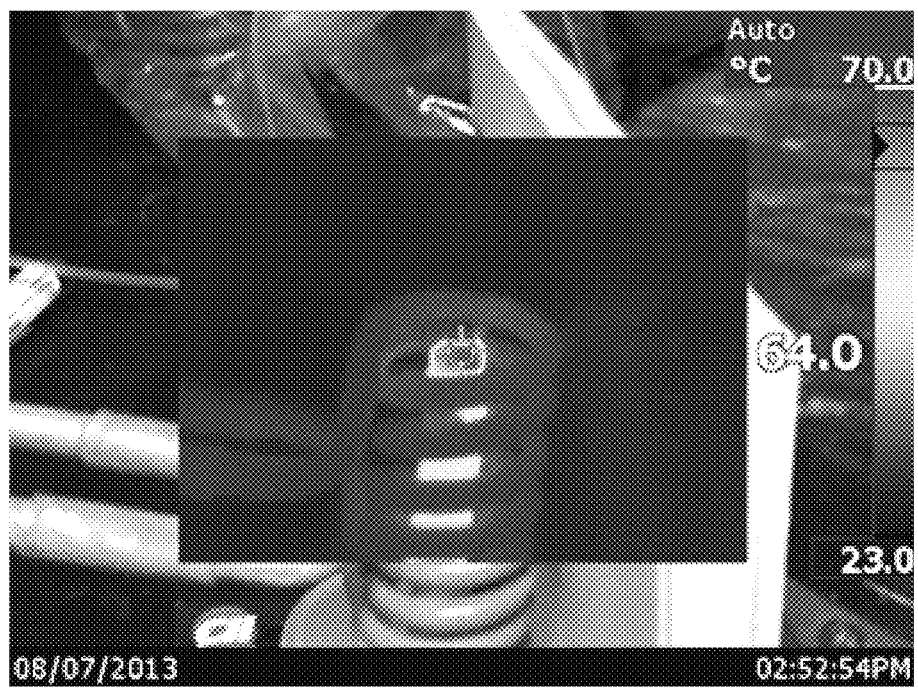
FIG. 4 provides thermo-imaging of the magnetic calcium phosphate nanoparticle bone cement formulation confirming the observed temperature increase in the bone cement.

MMA was mixed with BPO, NDMT, PMMA beads, and MCaP NPs (e.g., 0.41 g BPO, 5 mL MMA, 1.965 g PMMA beads, 0.786 g MCaP NPs, 30 µL NDMT). This mixture became an injectable paste and was loaded inside a Teflon tube and the polymerization process was further completed by inductive heating using an alternating current magnetic field. As shown in FIG. 4, infrared thermo imaging confirmed that the AC magnetic field triggered a temperature increase of the bone cement with an observed surface temperature up to 64° C. By adjusting the coil size, frequency and current, the temperature of the bone cement could be conveniently controlled. Accordingly, the above confirmed that MCaP NPs will, upon exposure to an AC magnetic field, generate heat that can be relied upon to promote polymerization and solidification of the bone cement formulations herein.

2. Commercial Bone Cement Formulation

For comparison, a standard bone cement sample was prepared by first weighing out 0.8% benzoyl peroxide (BPO) into a vial. Then, 25% (w/w) PMMA microsphere powder was weighed out and added to the vial. Then, methyl methacrylate (MMA) monomer solution was introduced into the vial and the vial was vortexed to completely dissolve all BPO. Note: the PMMA beads will not completely dissolve within half an hour. Once the BPO was dissolved, the appropriate amount of N,N-dimethyl-4-toluidine (DMT) was added to each sample. For a 5 mL sample, 1.85% DMT (e.g., 87 µL) allowed complete polymerization at room temperature within 1 hour.

3. Preparation and Comparison of Commercial Bone Cement and Bone Cement Containing MCaP NPs (ASTM F451-08)

Using a PTFE mold as specified in ASTM F45-08, Standard Specification for Acrylic Bone Cement (Current edition approved Aug. 1, 2008), bone cement containing MCaP NPs and a commercial cement were prepared and evaluated.

Microcomputed Tomography (Micro-CT)

Specimens were imaged using a microcomputed tomography (microCT) system and reconstructed with dimensionally-isotropic voxels (32×32×32 microns3). Image data was cropped to isolate individual specimens. Specimen image data was segmented using an iterative method to determine upper and lower image intensity bounds that separated the specimen data from background data. Cylindrical volumes of interest were selected for each set of imaging data and specimen volume fraction was determined as the sum of all voxels representing the specimen divided by the sum of all voxels within the cylindrical volume of interest.

It was therefore observed that commercial bone cement supplemented with PMMA beads has non-uniform pores (black) inside. FIG. 5A. Bone cement with MCaP NPs appears to form a relatively uniform matrix, with several white patches due to aggregates of MCaP NPs. FIG. 5B. The microCT image was taken under similar conditions and the background was adjusted to the same intensity. The brightness of bone cement specimens containing MCaP NPs is much higher than bone cements without MCaP NPs. This suggests that the addition of MCaP NPs significantly enhanced the radio-opacity of bone cement, allowing for relatively easier x-ray imaging procedures.

Mechanical Testing

Test methods for determining compressive properties of PMMA samples were based on ASTM F451-08: specimens were loaded in monotonic compression under displacement control (25.4 mm/sec). Specimens were compressed between two polished steel platens (Insight electromechanical testing system, MTS Corp., Eden Prairie, Minn.). Load and displacement data were recorded and converted to stress and strain by dividing by specimen cross-sectional area and length, respectively. The elastic region was identified within the stress-strain data by using a moving window approach (minimum window size of 0.45 seconds=45 data points) to detect any reduction in the slope of the stress-strain data. Elastic modulus for each specimen was determined as the slope of the stress-strain data within the elastic region. Peak stress was determined as the point of maximum stress. Toughness was determined as the area under the stress-strain curve prior to the point of peak stress.

Figure 6A:
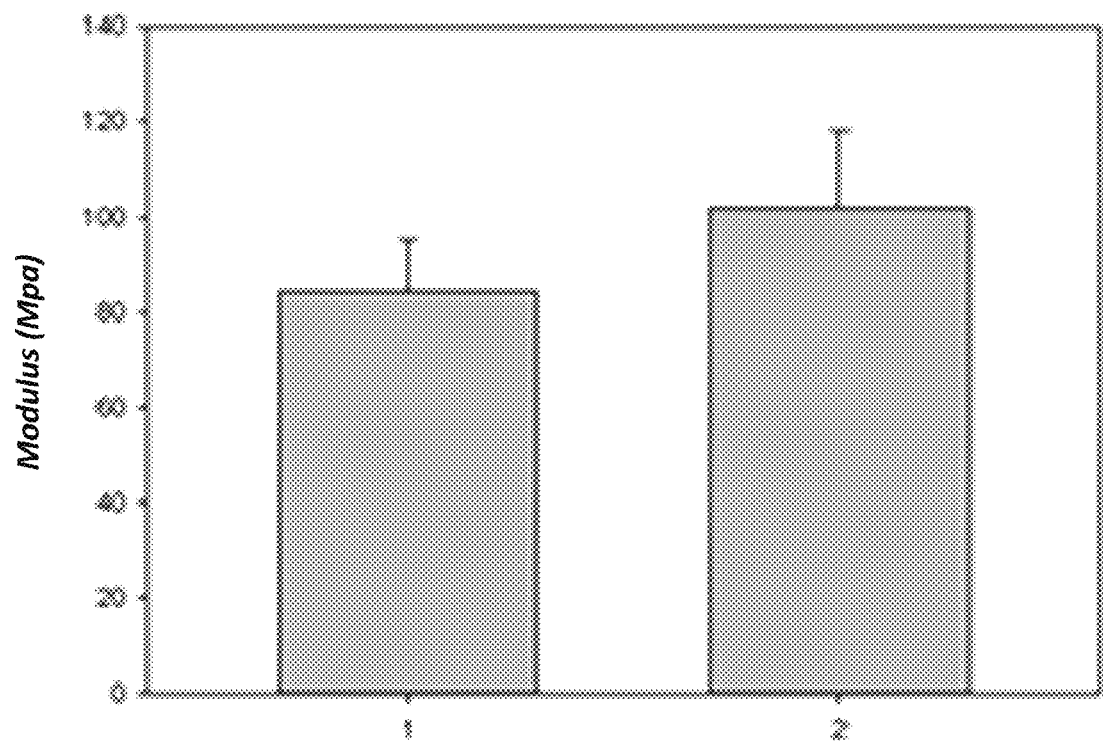
FIG. 6A illustrates the modulus value of (1) commercial bone cement and (2) bone cement containing magnetic calcium nanoparticles are described herein.
Figure 6B:
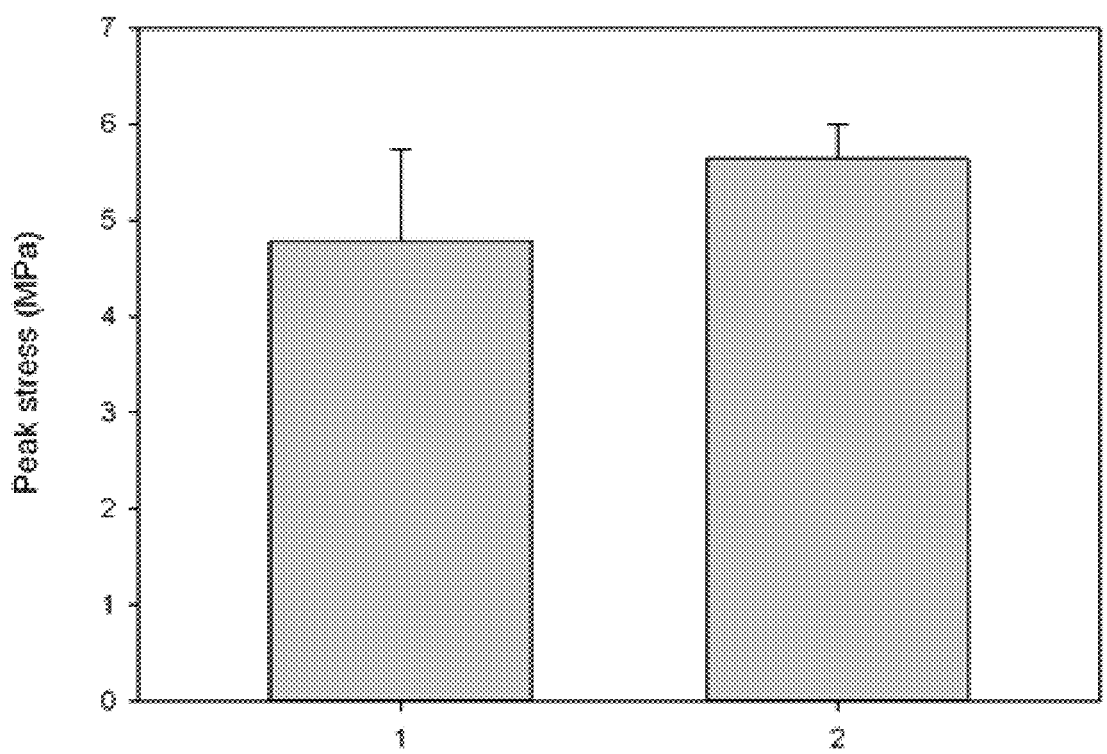
FIG. 6B illustrates the peak stress value of (1) commercial bone cement and (2) bone cement containing magnetic calcium nanoparticles as described herein.

As can be seen, both modulus (FIG. 6A) and peak stress (FIG. 6B) of new bone cement (sample 2) are higher than commercial bone cement (sample 1). The difference in the mean values of the two groups is greater than would be expected by chance; there is a statistically significant difference between modulus (P=0.025).

Cell Testing

ATCC Mc3T3 E1 Subclone 4 cell line (passage 2 from frozen) was used to evaluate the osteoconductivity, adherence (as an indication of osteointegration), and biocompatibility of various bone cement samples. These mouse preosteoblasts (http://www.atcc.org/products/all/CRL-2593.aspx) have behavior similar to primary calvarial osteoblasts. Media used for cell culture is made from α-MEM (Gibco, Cat #A10490-01), Fetal bovine Serum (FBS, ATCC Cat #30-2020), and Penicillin/Streptomycin (Fisher scientific, Cat #SV30010). Pure PMMA (Group A) was used as a control to bone cement containing MCaP NPs (Group B).

Figure 7:
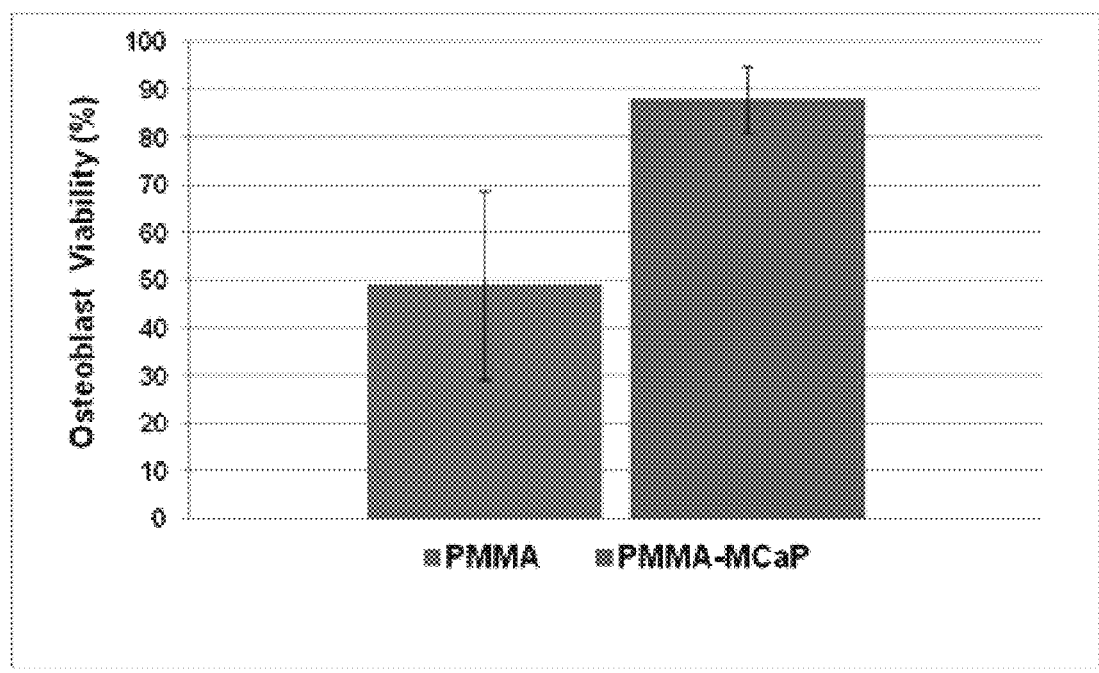
FIG. 7 illustrates osteoblast viability for PMMA and PMMA bone cement containing magnetic calcium phosphate nanoparticles.

Cell seeding and viability testing on bone cement samples placed inside non-tissue culture plate 100,000 cells (passage 11) were seeded per sample in 400 ul suspension. It was allowed to sit for two hours allow cell attachment. Then fresh media was added to each well and changed every two days. At day 5, cell counting of live, adherent cells using an automated cell counter (Invitrogen) was performed. By using a non-tissue culture plate, we are examining the adherence capability of bone cement samples. Non adherence cells will eventually die. As shown in FIG. 7, bone cement containing MCaP NPs has significantly larger amount of viable cells than the control PMMA. The addition of MCaP NPs significantly enhanced the adhesion of cells, thus improving the viability.

Cell Seeding and Viability Test on Bone Cement Samples Placed Inside Tissue Culture Plate (TCP)

The bone cement samples were placed in TCP 6 well plates and then seeded with passage 11 MC3T3 cells in a volume of 200 ul cell suspension containing 200,000 cells. The samples were not transferred to a new 6 well plate after the 2 hour 'seeding time'. Cell imaging was performed after 48 hrs directly on bone cement samples, while cell counting was performed inside the wells. For live/dead cell imaging, 1 µL of calcein and 5 µL of ethidium homodimer-1 (ETHD-1) were added to 1 mL cell culture media. Calcein was used to image the live cells, while ETHD-1 was used to image the dead cells.

Figure 8A:
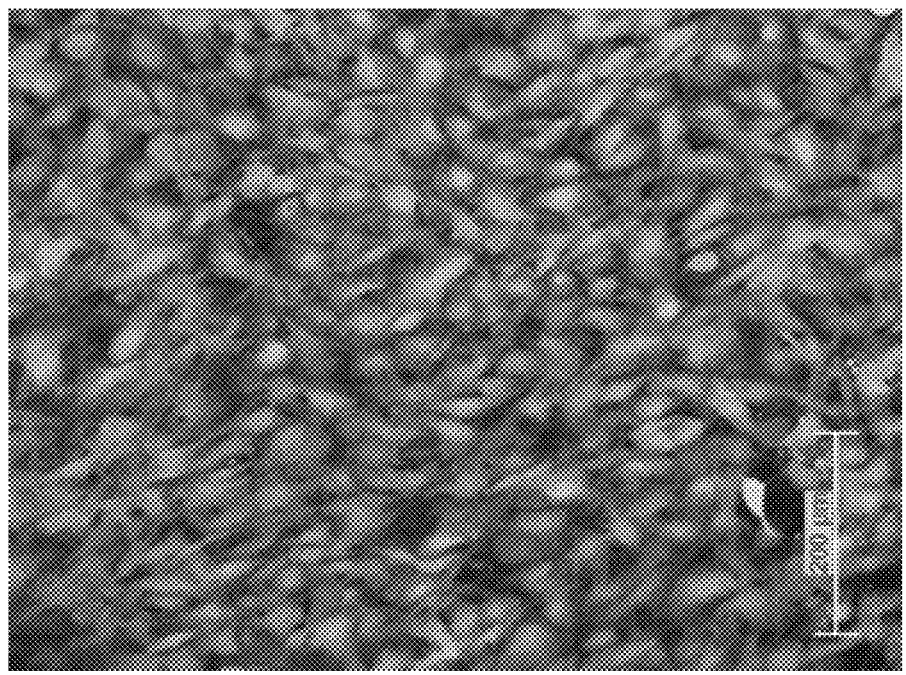
FIG. 8A provides cell imaging of a commercial PMMA bone cement.
Figure 8B:
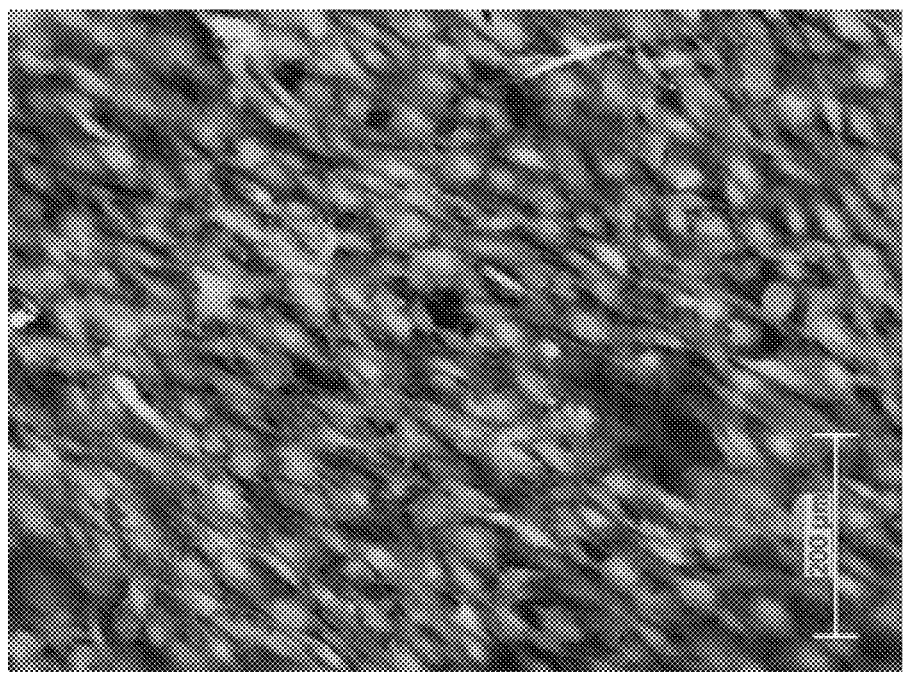
FIG. 8B provides cell imaging of a PMMA bone cement containing magnetic calcium phosphate nanoparticles.
Figure 8C:
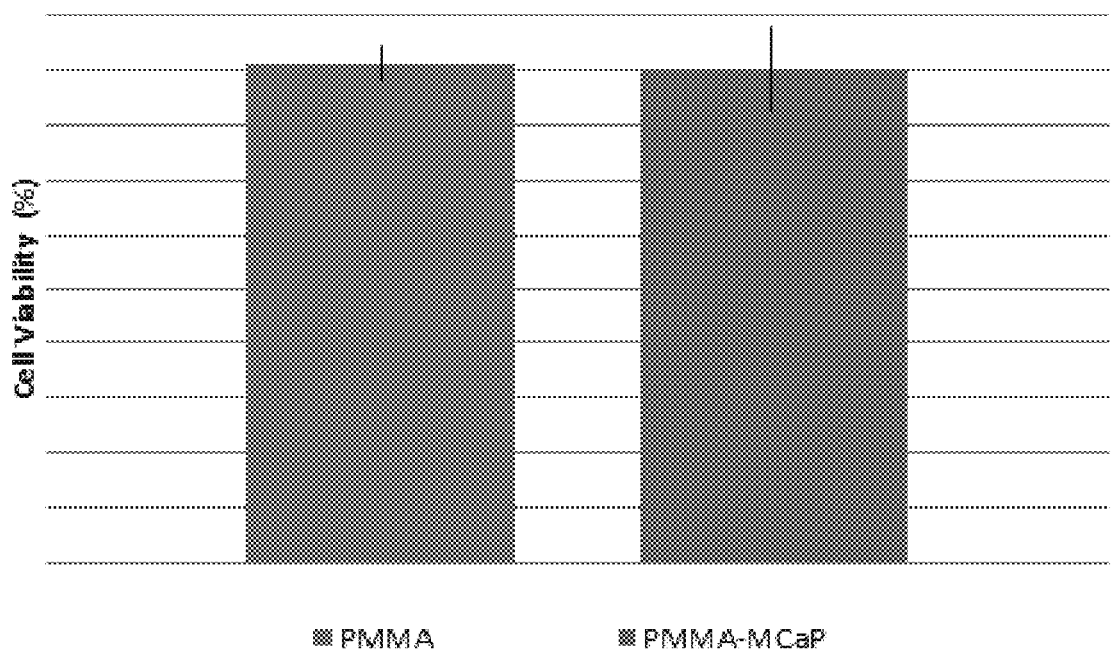
FIG. 8C illustrates cell viability of a commercial PMMA bone cement and PMMA bone cement containing magnetic calcium phosphate nanoparticles.

Results: live cell imaging indicating that bone cement containing MCaP NPs has relatively good cell biocompatibility. See FIG. 8A (control PMMA bone cement) and FIG. 8B (PMMA-MCaP NP based bone cement). The use of tissue culture plate greatly improved the viability of cells. Accordingly, both PMMA-MCaP NPs and PMMA samples had relatively good cell biocompatibility. See FIG. 8C where an automatic cell counter was employed to analyze cell viability.

The foregoing description is illustrative of particular embodiments of the invention but is not meant to be a limitation on the practice thereof. The following claims including all equivalents thereof are intended to define the scope of the invention.

The invention claimed is:

1. A method for fixing a prosthetic implant to a patient's bone which comprises applying a bone cement formulation to a prosthesis attachment site, said bone cement containing:
    a. magnetic calcium phosphate nanoparticles present in an amount of 5.0-95 wt. % and having a largest linear dimension of 150 nm to 50 microns;
    b. polymerizable acrylate monomer present in an amount of 5.0-95 wt. %;
    c. polyacrylate polymer present in an amount of 0-80 wt. % and having a largest linear dimension from 5.0 to 500 microns; and
    exposing said bone cement formulation to an alternating magnetic field and generating heat sufficient to promote polymerization of said polymerizable acrylate monomer, wherein said alternating magnetic field is at a frequency of 100 KHz at a field strength of 5 KA/m to 40 KA/m.

2. The method of claim 1 wherein said heat provides a temperature increase of said bone cement formulation to a temperature of 20° C. to 120° C.

3. The method of claim 1 including in said bone cement a polymerization chain initiator.

4. The method of claim 3 including in said bone cement an activator compound that promotes formation of free radicals from said polymerization chain initiator.

5. The method of claim 1 wherein said polymerizable acrylate monomer is selected from the group consisting of methyl methacrylate, butyl methacrylate, butyl methacrylate, triethylene glycol dimethacrylate, carbamate-methacrylate monomers, urethane dimethacrylate, bis-glycidyl methacrylate, ethyl methacrylate, isopropylmethacrylate, 2-hydroxyethyl methacrylate, 3-hydroxypropyl methacrylate, tetrahydrofurfuryl methacrylate, glycidyl methacrylate, 2-methoxyethyl methacrylate, 2-ethylhexyl methacrylate, benzyl methacrylate, 2,2-bis(methacryloxyphenyl)propane, 2,2-bis[4-(2-hydroxy-3-methacryloxypropoxy)phenyl]propane, 2,2-bis(4-methacryloxypolyethoxyphenyl)propane, ethylene glycol dimethacrylate, diethylene glycol dimethacrylate, butylene glycol dimethacrylate, N-vinyl pyrrolidone, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, methacrylic acid, octyl methacrylate, and pentaerythritol tetramethacrylate, and mixtures thereof.

6. The method of claim 1 including in said bone cement a radiopaque agent at a level of up to 15% by weight.

7. The method of claim 1 including in said bone cement a drug in an amount of 1.0 to 10.0% by weight.

8. The method of claim 1 including in said bone cement one or more of the following: carbon nanotubes, Au particles, MgO powders, Ti, $TiO_2$, hydroxyl apatite, fibers, and inorganic or organic particulate matter.

9. The method of claim 1 wherein said calcium phosphate particles comprise calcium phosphate and iron oxide.

10. A method for fixing a prosthetic implant to a patient's bone which comprises applying a bone cement formulation to a prosthesis attachment site, said bone cement containing:
   a. magnetic calcium phosphate nanoparticles present in an amount of 5.0-95 wt. % and having a largest linear dimension of 150 nm to 50 microns;
   b. polymerizable acrylate monomer present in an amount of 5.0-95 wt. %;
   c. polyacrylate polymer present in an amount of 0-80 wt. % and having a largest linear dimension from 5.0 to 500 microns; and
   polymerizing said acrylate monomer by exposing said bone cement formulation to an alternating magnetic field and generating heat sufficient to provide a temperature increase of said bone cement formulation of 20° C. to 120° C.

11. The method of claim 10 wherein said cement contains a chain polymerization initiator.

12. The method of claim 10, wherein said alternating magnetic field is at a frequency of 100 KHz to 980 KHz at a field strength of 5 KA/m to 40 KA/m.

13. The method of claim 11, including in said bone cement an activator compound that promotes formation of free radicals from said polymerization chain initiator.

14. The method of claim 10, wherein said polymerizable acrylate monomer is selected from the group consisting of methyl methacrylate, butyl methacrylate, butyl methacrylate, triethylene glycol dimethacrylate, carbamate-methacrylate monomers, urethane dimethacrylate, bis-glycidyl methacrylate, ethyl methacrylate, isopropylmethacrylate, 2-hydroxyethyl methacrylate, 3-hydroxypropyl methacrylate, tetrahydrofurfuryl methacrylate, glycidyl methacrylate, 2-methoxyethyl methacrylate, 2-ethylhexyl methacrylate, benzyl methacrylate, 2,2-bis(methacryloxyphenyl)propane, 2,2-bis[4-(2-hydroxy-3-methacryloxypropoxy)phenyl]propane, 2,2-bis(4-methacryloxypolyethoxyphenyl)propane, ethylene glycol dimethacrylate, diethylene glycol dimethacrylate, butylene glycol dimethacrylate, N-vinyl pyrrolidone, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, methacrylic acid, octyl methacrylate, and pentaerythritol tetramethacrylate, and mixtures thereof.

15. The method of claim 10, including in said bone cement a radiopaque agent at a level of up to 15% by weight.

16. The method of claim 10, including in said bone cement a drug in an amount of 1.0 to 10.0% by weight.

17. The method of claim 10, including in said bone cement one or more of the following: carbon nanotubes, Au particles, MgO powders, Ti, $TiO_2$, hydroxyl apatite, fibers, and inorganic or organic particulate matter.

18. The method of claim 10, wherein said calcium phosphate particles comprise calcium phosphate and iron oxide.

* * * * *